United States Patent
Umetani et al.

(10) Patent No.: US 8,344,156 B2
(45) Date of Patent: Jan. 1, 2013

(54) METHOD FOR PRODUCING FLUORINE-CONTAINING ACYLACETIC ACID DERIVATIVE, METHOD FOR PRODUCING FLUORINE-CONTAINING PYRAZOLECARBOXYLIC ACID ESTER DERIVATIVE, AND METHOD FOR PRODUCING FLUORINE-CONTAINING PYRAZOLECARBOXYLIC ACID DERIVATIVE

(75) Inventors: Hideki Umetani, Ritto (JP); Takeshi Kakimoto, Chiba (JP); Yoji Aoki, Chiba (JP)

(73) Assignee: Mitsui Chemicals Agro, Inc., Minato-Ku, Tokyo (JP)

( * ) Notice: Subject to any disclaimer, the term of this patent is extended or adjusted under 35 U.S.C. 154(b) by 2 days.

(21) Appl. No.: 12/922,959

(22) PCT Filed: Mar. 11, 2009

(86) PCT No.: PCT/JP2009/054602
§ 371 (c)(1),
(2), (4) Date: Sep. 16, 2010

(87) PCT Pub. No.: WO2009/116435
PCT Pub. Date: Sep. 24, 2009

(65) Prior Publication Data
US 2011/0015406 A1    Jan. 20, 2011

(30) Foreign Application Priority Data
Mar. 18, 2008   (JP) ................................. 2008-069937

(51) Int. Cl.
*C07D 231/10* (2006.01)
*C07C 229/00* (2006.01)

(52) U.S. Cl. ..................................... 548/374.1; 560/170

(58) Field of Classification Search ............... 548/374.1; 560/170
See application file for complete search history.

(56) References Cited

U.S. PATENT DOCUMENTS

| | | | |
|---|---|---|---|
| 6,706,911 B1 | 3/2004 | Lui et al. | |
| 2006/0252944 A1 | 11/2006 | Lantzsch et al. | |
| 2010/0274049 A1* | 10/2010 | Lui et al. ...................... | 562/553 |

FOREIGN PATENT DOCUMENTS

| | | |
|---|---|---|
| EP | 0 395 182 A1 | 10/1990 |
| GB | 2 310 661 A | 9/1997 |
| JP | 3-204845 A | 9/1991 |
| JP | 9-323953 A | 12/1997 |
| JP | 2005-511782 A | 4/2004 |
| JP | 2007-509850 A | 4/2007 |
| WO | WO 03/051820 A1 | 6/2003 |
| WO | WO 2005/042468 A1 | 5/2005 |
| WO | WO 2008/102678 A1 | 8/2008 |
| WO | WO 2009/083134 A1 | 7/2009 |

OTHER PUBLICATIONS

Lyga, John W. N-difluoromethylation of phenylazoles. Journal of Fluorine Chemistry. 92 (1998), 141-145.*
International Search Report (PCT/ISA/210) issued on Apr. 28, 2009, by Japanese Patent Office as the International Searching Authority for International Application No. PCT/JP2009/054602.
Written Opinion (PCT/ISA/237) issued on Apr. 28, 2009, by Japanese Patent Office as the International Searching Authority for International Application No. PCT/JP2009/054602.
Violetta Cecchetti et al., "Studies on 6-Aminoquinolones: Synthesis and Antibacterial Evaluation of 6-Amino-8-Methylquinolones", Journal of Medicinal Chemistry, 1996, vol. 39, No. 2, pp. 436-445.
Extended European Search Report dated Oct. 10, 2012 in corresponding European Patent Application No. 09 723 280.5.
March, Jerry: "Advanced organic chemistry: reactions, mechanism, and structure, $4^{th}$ ed.", 1992, John Wiley & Sons; p. 437, XP002638870.
Office Action(Notice of Reasons for Rejection) from Japanese Patent Office dated Nov. 6, 2012 in corresponding Japanese Patent Application No. 2010-503843.
Kappe, Thomas et al.: "Sythese von Pyridonen aus Enaminen und Cyanessigsäuren[1] (Synthesis of Pyridones from Enamines and Cyanoacetic Acids[1] )", Monatshefte für Chemie, Aug./Sep. 1983, vol. 114, No. 8/9, pp. 953-963; ISSN 0026-9247, with English abstract.

* cited by examiner

*Primary Examiner* — Joseph K. McKane
*Assistant Examiner* — Samantha Shterengarts
(74) *Attorney, Agent, or Firm* — Buchanan Ingersoll & Rooney PC

(57) ABSTRACT

A halogenating agent is added to a mixture including a base, a fluoroalkylcarboxylic acid derivative and an acrylate derivative to produce a fluoroaclyacetic acid derivative represented by the following Formula (3):

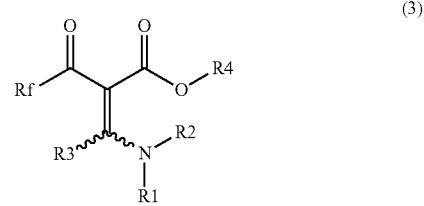

(3)

wherein Rf represents a fluorine containing alkyl group, R1 and R2 represent a hydrogen atom, an alkyl group, a cycloalkyl group, an aryl group, an arylalkyl group or an acyl group, or together represent an atomic group that forms a 5- or 6-membered ring containing a nitrogen atom to which R1 and R2 are bonded; R3 represents a hydrogen atom, an alkyl group, a cycloalkyl group, an aryl group, or an arylalkyl group; and R4 represents an alkyl group, a cycloalkyl group, an aryl group, or an aryl alkyl group.

9 Claims, No Drawings

METHOD FOR PRODUCING FLUORINE-CONTAINING ACYLACETIC ACID DERIVATIVE, METHOD FOR PRODUCING FLUORINE-CONTAINING PYRAZOLECARBOXYLIC ACID ESTER DERIVATIVE, AND METHOD FOR PRODUCING FLUORINE-CONTAINING PYRAZOLECARBOXYLIC ACID DERIVATIVE

TECHNICAL FIELD

The present invention relates to a method for producing a fluorine-containing acylacetic acid derivative, and a method for producing a fluorine-containing pyrazolecarboxylic acid ester derivative and a method for producing a fluorine-containing pyrazolecarboxylic acid derivative, using the same fluorine-containing acylacetic acid derivative.

BACKGROUND ART

Heterocyclic compounds into which a fluorine atom has been introduced are used in pharmaceuticals and agrochemicals because these compounds may remarkably improve physiological activity or the like. For these reasons, various technologies regarding fluorine-containing heterocyclic compounds are being developed. Among them, it is known that a fluorine-containing acylacetic acid derivative represented by ethyl 3-(N,N-dimethyl amino)-2-trifluoroacetylacrylate or the like can be converted to a fluorine-containing pyrazole derivative which is used in agricultural/horticultural germicides and the like, and may serve as an important production intermediate of the fluorine-containing heterocyclic compound.

As a representative example of conventional arts relating to the fluorine-containing acylacetic acid derivative, there is a method for producing a fluorine-containing acylacetic acid derivative by reacting a fluorine-containing alkyl carboxylic acid anhydride derivative with an acrylic ester derivative (for example, see Patent Literature 1).
Patent Literature 1: Japanese National Publication No. 2005-511782.

DISCLOSURE OF INVENTION

Problem to be Solved by the Invention

In the production method disclosed in Patent Literature 1, (1) an alkyl carboxylic acid anhydride such as trifluoroacetic anhydride, or (2) an acid chloride such as trifluoroacetyl chloride is shown as the fluorine-containing alkyl carboxylic acid anhydride derivative, and there are the following problems. In (1), out of two trifluoroacetyl groups present in the structure of the trifluoroacetic anhydride, only one trifluoroacetyl group is used in the reaction. As a result, a precious fluorine source is not effectively used. In (2), trifluoroacetyl chloride is gaseous at room temperature or is readily decomposable by reaction with water, thus result in poor handleability.

On the other hand, trifluoroacetic acid does not contain a fluorine atom not effectively used in the structure, is liquid at room temperature, and is stable with respect to moisture. Therefore, if a fluorine-containing acylacetic acid derivative can be produced using, as a starting material, a fluorine-containing alkyl carboxylic acid derivative with trifluoroacetic acid as a prominent example, in place of the fluorine-containing alkyl carboxylic acid anhydride described in Patent Literature 1, it is possible to overcome the above-mentioned problems.

The present invention is intended to provide a method for producing a fluorine-containing acylacetic acid derivative using a fluorine-containing alkyl carboxylic acid derivative, and a method for producing a fluorine-containing pyrazolecarboxylic acid ester derivative and a method for producing a fluorine-containing pyrazolecarboxylic acid derivative using the fluorine-containing acylacetic acid derivative, which are convenient and enable industrial-scale production.

Means for Solving Problems

As a result of extensive research in order to solve the above-described problems, it was found that a fluorine-containing acylacetic acid derivative was prepared by adding a halogenating agent to a mixture containing a fluorine-containing alkyl carboxylic acid derivative and an acrylic ester derivative, in the presence of a base. Further, the resulting fluorine-containing acylacetic acid derivative can be converted into a fluorine-containing pyrazole derivative via cyclization with an alkyl hydrazine derivative, followed by hydrolysis. The present invention has been completed based on these findings.

That is, the invention is as shown below.

1. A method for producing a fluorine-containing acylacetic acid derivative represented by the following Formula (3), comprising obtaining a mixture containing a base, a compound represented by the following Formula (1), and a compound represented by the following Formula (2), and adding a halogenating agent to the mixture:

wherein Rf represents an alkyl group having 1 to 6 carbon atoms which is substituted by at least one fluorine atom;

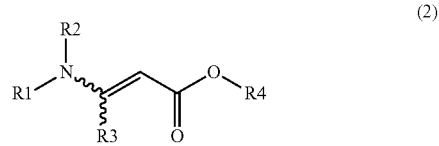

wherein R1 and R2 each independently represent a hydrogen atom, an alkyl group having 1 to 6 carbon atoms, a cycloalkyl group having 3 to 6 carbon atoms, an aryl group which may be substituted, an arylalkyl group which may be substituted, or an acyl group having 1 to 6 carbon atoms which may be substituted, or together represent an atomic group that forms a 5- or 6-membered ring containing 0 or 1 hetero atom with the nitrogen atom to which R1 and R2 are bonded; R3 represents a hydrogen atom, an alkyl group having 1 to 6 carbon atoms, a cycloalkyl group having 3 to 6 carbon atoms, an aryl group which may be substituted, or an arylalkyl group which may be substituted; and R4 represents an alkyl group having 1 to 6 carbon atoms, a cycloalkyl group having 3 to 6 carbon atoms, an aryl group which may be substituted, or an arylalkyl group which may be substituted;

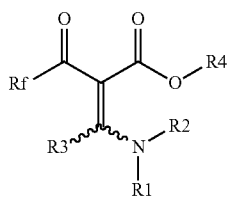

(3)

wherein Rf, R1, R2, R3 and R4 have the same definitions as above.

2. The method for producing a fluorine-containing acylacetic acid derivative according to 1, wherein R1 and R2 each independently represent an alkyl group having 1 to 6 carbon atoms or a cycloalkyl group having 3 to 6 carbon atoms, or together represent an atomic group that forms a 5- or 6-membered ring containing 0 or 1 hetero atom with the nitrogen atom to which R1 and R2 are bonded; and R3 represents a hydrogen atom.

3. The method for producing a fluorine-containing acylacetic acid derivative according to 2, wherein Rf represents a trifluoromethyl group, R1 and R2 respectively represent a methyl group, and R4 represents an alkyl group having 1 to 6 carbon atoms.

4. A method for producing a fluorine-containing pyrazolecarboxylic acid ester derivative represented by the following Formula (5), including reacting the compound represented by the following Formula (3) and prepared according to the fluorine-containing acylacetic acid derivative producing method of 1, with a compound represented by the following Formula (4):

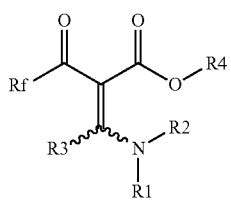

(3)

wherein Rf represents an alkyl group having 1 to 6 carbon atoms which is substituted by at least one fluorine atom; R1 and R2 each independently represent a hydrogen atom, an alkyl group having 1 to 6 carbon atoms, a cycloalkyl group having 3 to 6 carbon atoms, an aryl group which may be substituted, an arylalkyl group which may be substituted, or an acyl group having 1 to 6 carbon atoms which may be substituted, or together represent an atomic group that forms a 5- or 6-membered ring containing 0 or 1 hetero atom with the nitrogen atom to which R1 and R2 are bonded; R3 represents a hydrogen atom, an alkyl group having 1 to 6 carbon atoms, a cycloalkyl group having 3 to 6 carbon atoms, an aryl group which may be substituted, or an arylalkyl group which may be substituted; and R4 represents an alkyl group having 1 to 6 carbon atoms, a cycloalkyl group having 3 to 6 carbon atoms, an aryl group which may be substituted, or an arylalkyl group which may be substituted;

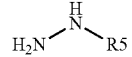

(4)

wherein R5 represents an alkyl group having 1 to 6 carbon atoms, a cycloalkyl group having 3 to 6 carbon atoms, an aryl group which may be substituted, or an arylalkyl group which may be substituted;

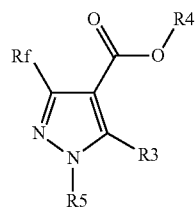

(5)

wherein Rf, R3, R4 and R5 have the same definitions as above.

5. The method for producing a fluorine-containing pyrazolecarboxylic acid ester derivative according to 4, wherein R1 and R2 each independently represent an alkyl group having 1 to 6 carbon atoms or a cycloalkyl group having 3 to 6 carbon atoms, or together represent an atomic group that forms a 5- or 6-membered ring containing 0 or 1 hetero atom with the nitrogen atom to which R1 and R2 are bonded; and R3 represents a hydrogen atom.

6. The method for producing a fluorine-containing pyrazolecarboxylic acid ester derivative according to 5, wherein Rf represents a trifluoromethyl group, R1 and R2 respectively represent a methyl group, R4 represents an alkyl group having 1 to 6 carbon atoms, and R5 represents an alkyl group having 1 to 6 carbon atoms.

7. A method for producing a fluorine-containing pyrazolecarboxylic acid derivative represented by the following Formula (6), including hydrolyzing the compound represented by the following Formula (5) and prepared according to the fluorine-containing pyrazolecarboxylic acid ester derivative production method of 4:

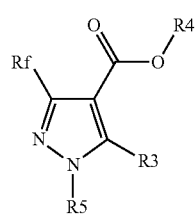

(5)

wherein Rf represents an alkyl group having 1 to 6 carbon atoms which is substituted by at least one fluorine atom; R3 represents a hydrogen atom, an alkyl group having 1 to 6 carbon atoms, a cycloalkyl group having 3 to 6 carbon atoms, an aryl group which may be substituted, or an arylalkyl group which may be substituted; R4 represents an alkyl group having 1 to 6 carbon atoms, a cycloalkyl group having 3 to 6 carbon atoms, an aryl group which may be substituted, or an arylalkyl group which may be substituted; and R5 represents an alkyl group having 1 to 6 carbon atoms, a cycloalkyl group having 3 to 6 carbon atoms, an aryl group which may be substituted, or an arylalkyl group which may be substituted;

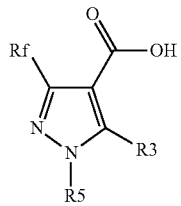

(6)

wherein Rf, R3, and R5 have the same definitions as above.

8. The method for producing a fluorine-containing pyrazolecarboxylic acid derivative according to 7, wherein, R1 and R2 each independently represent an alkyl group having 1 to 6 carbon atoms, or a cycloalkyl group having 3 to 6 carbon atoms, or together represent an atomic group that forms a 5- or 6-membered ring containing 0 or 1 hetero atom with the nitrogen atom to which R1 and R2 are bonded; and R3 represents a hydrogen atom.

9. The method for producing a fluorine-containing pyrazolecarboxylic acid derivative according to 8, wherein Rf represents a trifluoromethyl group, R1 and R2 respectively represent a methyl group, R4 represents an alkyl group having 1 to 6 carbon atoms, and R5 represents an alkyl group having 1 to 6 carbon atoms.

Effects of the Invention

According to the present invention, a method for producing a fluorine-containing acylacetic acid derivative using a fluorine-containing alkyl carboxylic acid derivative, and a method for producing a fluorine-containing pyrazolecarboxylic acid ester derivative and a method for producing a fluorine-containing pyrazolecarboxylic acid derivative using the fluorine-containing acylacetic acid derivative, which are convenient and enable industrial-scale production may be provided.

BEST MODE FOR CARRYING OUT THE INVENTION

In the following, the invention will be described in detail.

The method for producing a fluorine-containing acylacetic acid derivative represented by the following Formula (3) in accordance with the present invention is characterized by using a base, a compound represented by the following Formula (1), a compound represented by the following Formula (2), and a halogenating agent. Specifically, the present invention provides a method for producing a fluorine-containing acylacetic acid derivative represented by the following Formula (3), including obtaining a mixture containing a base, a compound represented by the following Formula (1), and a compound represented by the following Formula (2), and adding a halogenating agent to the mixture.

The process of adding a halogenating agent in the present invention may include a process of further adding at least one selected from a base, a compound represented by the following Formula (1), and a compound represented by the following Formula (2).

The addition of the halogenating agent at the last stage is an important feature of the present invention, whereby it becomes possible to promote the desired reaction with a good yield.

Further, the method for producing a fluorine-containing acylacetic acid derivative represented by the following Formula (3) in accordance with the present invention may further include other processes such as a post-treatment process, if necessary, in addition to the above-mentioned processes.

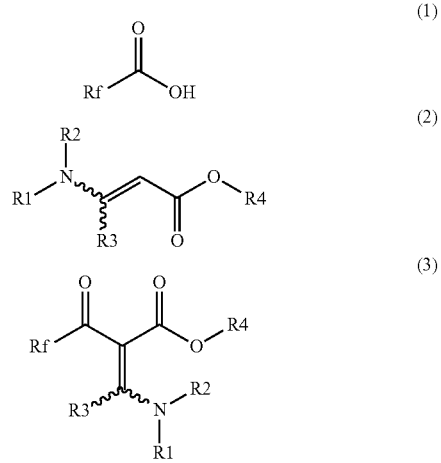

In the Formula, Rf represents an alkyl group having 1 to 6 carbon atoms, which is substituted by at least one fluorine atom. R1 and R2 each independently represent a hydrogen atom, an alkyl group having 1 to 6 carbon atoms, a cycloalkyl group having 3 to 6 carbon atoms, an aryl group which may be substituted, an arylalkyl group which may be substituted, or an acyl group having 1 to 6 carbon atoms which may be substituted, or together represent an atomic group that forms a 5- or 6-membered ring containing 0 or 1 hetero atom with the nitrogen atom to which R1 and R2 are bonded. R3 represents a hydrogen atom, an alkyl group having 1 to 6 carbon atoms, a cycloalkyl group having 3 to 6 carbon atoms, an aryl group which may be substituted, or an arylalkyl group which may be substituted. R4 represents an alkyl group having 1 to 6 carbon atoms, a cycloalkyl group having 3 to 6 carbon atoms, an aryl group which may be substituted, or an arylalkyl group which may be substituted.

In the present invention, at least one base is used. In the following, the base will be described in detail.

The base used in the present invention may be an organic base or an inorganic base. Specific examples of the organic base include tertiary amines, such as triethylamine, tributylamine, trioctylamine, diisopropylethylamine, 1,4-diazabicyclo[2.2.2]octane, and 1,8-diazabicyclo[5.4.0]-7-undecene, and aromatic amines, such as pyridine, collidine, lutidine, and 4-dimethylaminopyridine. Specific examples of the inorganic base include sodium hydrogen carbonate, potassium hydrogen carbonate, sodium carbonate, and potassium carbonate. These bases may be used singularly or in a mixture of two or more kinds at an arbitrary ratio.

The equivalent of the base to be used is not particularly limited insofar as it is 2 equivalents or more with respect to the compound represented by Formula (1). From an economical viewpoint, the amount of the base is preferably 2 equivalents or more and 5 equivalents or less to the compound represented by Formula (1).

In the following, a compound represented by Formula (1) will be described.

Rf in Formula (1) represents an alkyl group having 1 to 6 carbon atoms, which is substituted by at least one fluorine atom. The alkyl group having 1 to 6 carbon atoms may be either a straight-chain alkyl group or branched alkyl group. Examples thereof include straight-chain alkyl groups such as a methyl group, an ethyl group, a propyl group, a butyl group, a pentyl group, or a hexyl group and branched alkyl groups such as an isopropyl group, an isobutyl group, a sec-butyl group, a 1-methylbutyl group, a 2-methylbutyl group, a 3-methylbutyl group, a 1,1-dimethylpropyl group, a 2,2-dimethylpropyl group, a 1,2-dimethylpropyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, or a 3,3-dimethylbutyl group.

Rf in Formula (1) may be any of these alkyl groups having 1 to 6 carbon atoms as long as they are substituted by at least one fluorine atom. Examples thereof include perfluoroalkyl groups such as a trifluoromethyl group, a pentafluoroethyl group, a heptafluoropropyl group, a heptafluoroisopropyl group, or a nonafluorobutyl group, fluoroalkyl groups having a hydrogen atom such as a monofluoromethyl group, or a difluoromethyl group, or fluoroalkyl groups having a fluorine atom and another halogen atom such as a chlorodifluoromethyl group, or a bromodifluoromethyl group.

A compound represented by Formula (1) may be a commercially available one or one produced according to a known method.

The Rf in the invention is preferably a fluoroalkyl group selected from a trifluoromethyl group, a difluoromethyl group, a chlorodifluoromethyl group, a pentafluoroethyl group, and a heptafluoropropyl group, a trifluoromethyl group or difluromethyl group being more preferred.

In the following, a compound represented by Formula (2) will be described.

R1 and R2 in Fomula (2) each independently represent a hydrogen atom, an alkyl group having 1 to 6 carbon atoms, a cycloalkyl group having 3 to 6 carbon atoms, an aryl group which may be substituted, an arylalkyl group which may be substituted, or an acyl group having 1 to 6 carbon atoms which may be substituted, or together represent an atomic group that forms a 5- or 6-membered ring containing 0 or 1 hetero atom with the nitrogen atom to which R1 and R2 are bonded An alkyl group having 1 to 6 carbon atoms in the R1 and R2 in Fomula (2) has the same definitions as that of the alkyl group having 1 to 6 carbon atoms in the Rf in Formula (1).

A cycloalkyl group having 3 to 6 carbon atoms in the R1 and R2 in Formula (2) represents a cyclopropyl group, a cyclobutyl group, a cyclopentyl group or a cyclohexyl group.

Examples of the substituent for the aryl group which may be substituted, the arylalkyl group which may be substituted and the acyl group having 1 to 6 carbon atoms which may be substituted for R1 and R2 in Formula (2) include an alkyl group, such as a methyl group, an ethyl group, a propyl group, an isopropyl group, a butyl group, an isobutyl group, a sec-butyl group, or a tert-butyl group; a cycloalkyl group, such as a cyclopropyl group, a cyclobutyl group, a cyclopentyl group, or a cyclohexyl group; a halogen-substituted alkyl group, such as a trifluoromethyl group, a pentafluoroethyl group, a hexafluoropropyl group, a hexafluoroisopropyl group, a trifluoroethyl group, a difluoromethyl group, a chlorodifluoromethyl group, a bromodifluoromethyl group, or a monofluoromethyl group; an aryl group, such as a phenyl group; an arylalkyl group, such as a benzyl group;

an alkoxy group, such as a methoxy group, an ethoxy group, a propoxy group, an isopropoxy group, a butoxy group, an isobutoxy group, a sec-butoxy group, or a tert-butoxy group; a cycloalkoxy group, such as a cyclopropoxy group, a cyclobutoxy group, a cyclopentyloxy group, or a cyclohexyloxy group; a halogen-substituted alkoxy group, such as a trifluoromethoxy group, a difluoromethoxy group, a trifluoroethoxy group, or a trichloroethoxy group; an aryloxy group, such as a phenoxy group; an arylalkyloxy group, such as a benzyloxy group; an alkoxycarbonyl group, such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, or a tert-butoxycarbonyl group; a cycloalkoxycarbonyl grop, such as a cyclopropoxycarbonyl group, a cyclobutoxycarbonyl group, a cyclopentyloxycarbonyl group, or a cyclohexyloxycarbonyl group; a halogen-substituted alkoxycarbonyl group, such as a trifluoromethoxycarbonyl group, a difluoromethoxycarbonyl group, a trifluoroethoxycarbonyl group, or a trichloroethoxycarbonyl group; an aryloxycarbonyl group, such as a phenoxycarbonyl group; an arylalkyloxycarbonyl group, such as benzyloxycarbonyl group;

an alkylthio group, such as a methylthio group, an ethylthio group, a propylthio group, or a butylthio group; a cycloalkylthio group, such as a cyclopropylthio group, a cyclobutylthio group, a cyclopentylthio group, or a cyclohexylthio group; a halogen-substituted alkylthio group such as a trifluoromethylthio group, a difluoromethylthio group, or a trifluoroethylthio group; an arylthio group, such as a phenylthio group; an arylalkylthio group, such as a benzylthio group; an alkylsulfinyl group, such as a methanesulfinyl group, an ethanesulfinyl group, a propanesulfinyl group, or a butanesulfinyl group; a cycloalkylsulfinyl group, such as a cyclopropanesulfinyl group, a cyclobutanesulfinyl group, a cyclopentanesulfinyl group, or a cyclohexanesulfinyl group; a halogen-substituted alkylsulfinyl group, such as a trifluoromethanesulfinyl group, a difluoromethanesulfinyl group, or a trifluoroethanesulfinyl group; an arylsulfinyl group, such as a phenylsulfinyl group; an aryalkylsulfinyl group, such as a benzylsulfinyl group; an alkylsulfonyl group, such as a methanesulfonyl group, an ethanesulfonyl group, a propanesulfonyl group, or a butanesulfonyl group; a cycloalkylsulfonyl group, such as a cyclopropanesulfonyl group, a cyclobutanesulfonyl group, a cyclopentanesulfonyl group, or a cyclohexanesulfonyl group; a halogen-substituted alkylsulfonyl group, such as a trifluoromethanesulfonyl group, a difluoromethanesulfonyl group, or a trifluoroethanesulfonyl group; an arylsulfonyl group, such as a phenylsulfonyl group; an arylalkylsulfonyl group, such as a benzylsulfonyl group;

an alkylcarbonyl group, such as a methylcarbonyl group, an ethylcarbonyl group, a propylcarbonyl group, an isopropylcarbonyl group, a butylcarbonyl group, an isobutylcarbonyl group, a sec-butylcarbonyl group, or a tert-butylcarbonyl group; a cycloalkylcarbonyl group, such as a cyclopropylcarbonyl group, a cyclobutylcarbonyl group, a cyclopropylcarbonyl group, a cyclopentylcarbonyl group, or a cyclohexylcarbonyl group; a halogen-substituted alkylcarbonyl group, such as a trifluoromethanecarbonyl group, a difluoromethanecarbonyl group, or a trichloromethanecarbonyl group; an arylcarbonyl group, such as a benzoyl group; an alkylcarbonyloxy group, such as a methylcarbonyloxy group, an ethylcarbonyloxy group, a propylcarbonyloxy group, an isopropylcarbonyloxy group, a butylcarbonyloxy group, an isobutylcarbonyloxy group, a sec-butylcarbonyloxy group, or a tert-butylcarbonyloxy group; a cycloalkylcarbonyloxy group, such as cyclopropylcarbonyloxy group, a cyclobutylcarbonyloxy group, a cyclopropylcarbonyloxy group, a cyclopentylcarbonyloxy group, or a cyclohexylcarbonyloxy group; an arylcarbonyloxy group, such as a benzoyloxy group;

an alkylcarbonylamino group, such as a methylcarbonylamino group, an ethylcarbonylamino group, a propylcarbonylamino group, an isopropylcarbonylamino group, a butylcarbonylamino group, an isobutylcarbonylamino group, a sec-butylcarbonylamino group, or a tert-butylcarbonylamino group; a cycloalkylcarbonylamino group, such as a cyclopropylcarbonylamino group, a cyclobutylcarbonylamino group, a cyclopropylcarbonylamino group, a cyclopentylcarbonylamio group or a cyclohexylcarbonylamino group; an arylcarbonylamino group, such as a benzoylamino group; an alkoxycarbonylamino group, such as a methoxycarbonylamino group, an ethoxycarbonylamino group, a propoxycarbonylamino group, an isopropoxycarbonylamino group, a butoxycarbonylamino group, an isobutoxycarbonylamino group, a sec-butoxycarbonylamino group, a tert-butoxycarbonylamino group, a methoxycarbonyl(methyl)amino group, an ethoxycarbonyl(methyl)amino group, a propoxycarbonyl(methyl)amino group, an isopropoxycarbonyl(methyl)amino group, a butoxycarbonyl(methyl)amino group, an isobutoxycarbonyl(methyl)amino group, a sec-butoxycarbonyl(methyl)amino group, a tert-butoxycarbonyl(methyl)amino group, a methoxycarbonyl(ethyl)amino group, an ethoxycarbonyl(ethyl)amino group, a propoxycarbonyl(ethyl)amino group, an isopropoxycarbonyl(ethyl)amino group, a butoxycarbonyl(ethyl)amino group, an isobutoxycarbonyl(ethyl)amino group, a sec-butoxycarbonyl(ethyl)amino group, or a tert-butoxycarbonyl(ethyl)amino group; cycloalkoxycarbonylamino groups such as a cyclopropoxycarbonylamino group, a cyclobutoxycarbonylamino group, a cyclopentyloxycarbonylamino group, a cyclohexyloxycarbonylamino group, a cyclopropoxycarbonyl(methyl)amino group, a cyclobutoxycarbonyl(methyl)amino group, a cyclopentyloxycarbonyl(methyl)amino group, a cyclohexyloxycarbonyl(methyl)amino group, a cyclopropoxycarbonyl(ethyl) amino group, a cyclobutoxycarbonyl(ethyl)amino group, a cyclopentyloxycarbonyl(ethyl)amino group, or a cyclohexyloxycarbonyl(ethyl)amino group; a halogen-substituted alkoxycarbonylamino group, such as a trifluoromethoxycarbonylamino group, a difluoromethoxycarbonylamino group, a trifluoroethoxycarbonylamino group, a trichloroethoxycarbonylamino group, a trifluoromethoxycarbonyl(methyl) amino group, a difluoromethoxycarbonyl(methyl)amino group, a trifluoroethoxycarbonyl(methyl)amino group, a trichloroethoxycarbonyl(methyl)amino group, a trifluoromethoxycarbonyl(ethyl)amino group, a difluoromethoxycarbonyl(ethyl)amino group, a trifluoroethoxycarbonyl (ethyl)amino group, or a trichloroethoxycarbonyl(ethyl) amino group; an aryloxycarbonylamino group, such as a phenoxycarbonylamino group, a phenoxycarbonyl(methyl) amino group, or a phenoxycarbonyl(ethyl)amino group; an arylalkyloxycarbonylamino group, such as a benzyloxycarbonylamino group, a benzyloxycarbonyl(methyl)amino group or a benzyloxycarbonyl(ethyl)amino group;

an alkylaminocarbonyloxy group, such as a methylaminocarbonyloxy group, an ethylaminocarbonyloxy group, a propylaminocarbonyloxy group, an isopropylaminocarbonyloxy group, a butylaminocarbonyloxy group, an isobutylaminocarbonyloxy group, a sec-butylaminocarbonyloxy group, a tert-butylaminocarbonyloxy group, a dimethylaminocarbonyloxy group, an {ethyl(methyl)amino}carbonyloxy group, a {propyl(methyl)amino}carbonyloxy group, an {isopropyl(methyl)amino}carbonyloxy group, a {butyl(methyl)amino}carbonyloxy group, an {isobutyl(methyl)amino}carbonyloxy group, a {sec-butyl(methyl)amino}carbonyloxy group, a {tert-butyl(methyl)amino}carbonyloxy group, a diethylaminocarbonyloxy group, a {propyl(ethyl)amino}carbonyloxy group, an {isopropyl(ethyl)amino}carbonyloxy group, a {butyl(ethyl)amino}carbonyloxy group, an {isobutyl(ethyl)amino}carbonyloxy group, a {sec-butyl(ethyl)amino}carbonyloxy group, or a {tert-butyl(ethyl)amino}carbonyloxy group; a cycloalkylaminocarbonyloxy group, such as a cyclopropylaminocarbonyloxy group, a cyclobutylaminocarbonyloxy group, a cyclopentylaminocarbonyloxy group, a cyclohexylaminocarbonyloxy group, a {cyclopropyl(methyl)amino}carbonyloxy group, a {cyclobutyl(methyl)amino}carbonyloxy group, a {cyclopentyl(methyl)amino}carbonyloxy group, a {cyclohexyl(methyl)amino}carbonyloxy group, a {cyclopropyl(ethyl)amino}carbonyloxy group, a {cyclobutyl(ethyl)amino}carbonyloxy group, a {cyclopentyl(ethyl)amino}carbonyloxy group, or a {cyclohexyl(ethyl)amino}carbonyloxy group; a halogen-substituted alkylaminocarbonyloxy group, such as a trifluoromethylaminocarbonyloxy group, a difluoromethylaminocarbonyloxy group, a trifluoroethylaminocarbonyloxy group, a trichloroethylaminocarbonyloxy group, a {trifluoromethyl(methyl)amino}carbonyloxy group, a {difluoromethyl(methyl)amino}carbonyloxy group, a {trifluoroethyl(methyl)amino}carbonyloxy group, a {trichloroethyl(methyl)amino}carbonyloxy group, a {trifluoromethyl(ethyl)amino}carbonyloxy group, a {difluoromethyl(ethyl)amino}carbonyloxy group, a {trifluoroethyl(ethyl)amino}carbonyloxy group, or a {trichloroethyl(ethyl)amino}carbonyloxy group; an arylaminocarbonyloxy group, such as a phenylaminocarbonyloxy group, a {phenyl(methyl)amino}carbonyloxy group or a {phenyl(ethyl)amino}carbonyloxy group; an arylalkylaminocarbonyloxy group, such as a benzylaminocarbonyloxy group, a {benzyl(methyl)amino}carbonyloxy group, or a {benzyl(ethyl)aminocarbonyloxy group; a cyclic aminocarbonyloxy group, such as a pyrrolidinocarbonyloxy group, a piperidinocarbonyloxy group or a morpholinocarbonyloxy group;

an alkylaminocarbonylamino group, such as a methylaminocarbonylamino group, an ethylaminocarbonylamino group, a propylaminocarbonylamino group, an isopropylaminocarbonylamino group, a butylaminocarbonylamino group, an isobutylaminocarbonylamino group, a sec-butylaminocarbonylamino group, a tert-butylaminocarbonylamino group, a dimethylaminocarbonylamino group, an {ethyl(methyl)amino}carbonylamino group, a {propyl(methyl)amino}carbonylamino group, an {isopropyl(methyl)amino}carbonylmethyl group, a {butyl(methyl)amino}carbonylamino group, an {isobutyl(methyl)amino}carbonylamino group, a {sec-butyl(methyl)amino}carbonylamino group, a {tert-butyl(methyl)amino}carbonylamino group, a diethylaminocarbonylamino group, a {propyl(ethyl)amino}carbonylamino group, an {isopropyl(ethyl)amino}carbonylamino group, a {butyl(ethyl)amino}carbonylamino group, an {isobutyl(ethyl)amino}carbonylamino group, a {sec-butyl(ethyl)amino}carbonylamino group, a {tert-butyl(ethyl)amino}carbonylamino group, a methylaminocarbonyl(methyl)amino group, an ethylaminocarbonyl(methyl)amino group, a propylaminocarbonyl(methyl)amino group, an isopropylaminocarbonyl(methyl)amino group, a butylaminocarbonyl(methyl)amino group, an isobutylaminocarbonyl(methyl)amino group, a sec-butylaminocarbonyl(methyl)amino group, a tert-butylaminocarbonyl(methyl)amino group, a methylaminocarbonyl(ethyl)amino group, an ethylaminocarbonyl(ethyl)amino group, a propylaminocarbonyl(ethyl)amino group, an isopropylaminocarbonyl(ethyl)amino group, a butylaminocarbonyl(ethyl)amino group, an isobutylaminocarbonyl(ethyl)amino group, a sec-butylaminocarbonyl(ethyl)amino group, a tert-butylaminocarbonyl (ethyl)amino group, a dimethylaminocarbonyl(methyl) amino group, an {ethyl(methyl)amino}carbonyl(methyl) amino group, a {propyl(methyl)amino}carbonyl(methyl) amino group, an {isopropyl(methyl)amino}carbonyl (methyl)amino group, a {butyl(methyl)amino}carbonyl (methyl)amino group, an {isobutyl(methyl)amino}carbonyl (methyl)amino group, a {sec-butyl(methyl)amino}carbonyl (methyl)amino group, a {tert-butyl(methyl)amino}carbonyl (methyl)amino group, a dimethylaminocarbonyl(ethyl) amino group, an {ethyl(methyl)amino}carbonyl(ethyl) amino group, a {propyl(methyl)amino}carbonyl(ethyl) amino group, an {isopropyl(methyl)amino}carbonyl(ethyl) amino group, a {butyl(methyl)amino}carbonyl(ethyl)amino group, an {isobutyl(methyl)amino}carbonyl(ethyl)amino group, a {sec-butyl(methyl)amino}carbonyl(ethyl)amino group, a {tert-butyl(methyl)amino}carbonyl(ethyl)amino group, a diethylaminocarbonyl(methyl)amino group, an {ethyl(propyl)amino}carbonyl(methyl)amino group, an {ethyl(isopropyl)amino}carbonyl(methyl)amino group, a {butyl(ethyl)amino}carbonyl(methyl)amino group, an {ethyl(isobutyl)amino}carbonyl(methyl)amino group, a {sec-butyl(ethyl)amino}carbonyl(methyl)amino group, a {tert-butyl(ethyl)amino}carbonyl(methyl)amino group, a diethylaminocarbonyl(ethyl)amino group, an {ethyl(propyl) amino}carbonyl(ethyl)amino group, an {ethyl(isopropyl) amino}carbonyl(ethyl)amino group, an {ethyl(butyl) amino}carbonyl(ethyl)amino group, an {ethyl(isobutyl) amino}carbonyl(ethyl)amino group, a {sec-butyl(ethyl) amino}carbonyl(ethyl)amino group, or a {tert-butyl(ethyl) amino}carbonyl(ethyl)amino group;

a cycloalkylaminocarbonylamino group, such as a cyclopropylaminocarbonylamino group, a cyclobutylaminocarbonylamino group, a cyclopentylaminocarbonylamino group, a cyclohexylaminocarbonylamino group, a {cyclopropyl(methyl)amino}carbonylamino group, a {cyclobutyl(methyl) amino}carbonylamino group, a {cyclopentyl(methyl) amino}carbonylamino group, a {cyclohexyl(methyl) amino}carbonylamino group, a {cyclopropyl(ethyl) amino}carbonylamino group, a {cyclobutyl(ethyl) amino}carbonylamino group, a {cyclopentyl(ethyl) amino}carbonylamino group, a {cyclohexyl(ethyl) amino}carbonylamino group, a cyclopropylaminocarbonyl (methyl)amino group, a cyclobutylaminocarbonyl(methyl) amino group, a cyclopentylaminocarbonyl(methyl)amino group, a cyclohexylaminocarbonyl(methyl)amino group, a cyclopropylaminocarbonyl(ethyl)amino group, a cyclobutylaminocarbonyl(ethyl)amino group, a cyclopentylaminocarbonyl(ethyl)amino group, a cyclohexylaminocarbonyl(ethyl) amino group, a {cyclopropyl(methyl)amino}carbonyl (methyl)amino group, a {cyclobutyl(methyl)amino}carbonyl (methyl)amino group, a {cyclopentyl(methyl) amino}carbonyl(methyl)amino group, a {cyclohexyl (methyl)amino}carbonyl(methyl)amino group, a {cyclopropyl(methyl)amino}carbonyl(ethyl)amino group, a {cyclobutyl(methyl)amino}carbonyl(ethyl)amino group, a {cyclopentyl(methyl)amino}carbonyl(ethyl)amino group, a {cyclohexyl(methyl)amino}carbonyl(ethyl)amino group, a {cyclopropyl(ethyl)amino}carbonyl(methyl)amino group, a {cyclobutyl(ethyl)amino}carbonyl(methyl)amino group, a {cyclopentyl(ethyl)amino}carbonyl(methyl)amino group, a {cyclohexyl(ethyl)amino}carbonyl(methyl)amino group, a {cyclopropyl(ethyl)amino}carbonyl(ethyl)amino group, a {cyclobutyl(ethyl)amino}carbonyl(ethyl)amino group, a {cyclopentyl(ethyl)amino}carbonyl(ethyl)amino group, or a {cyclohexyl(ethyl)amino}carbonyl(ethyl)amino group;

a halogen-substituted alkylaminocarbonylamino group, such as a trifluoromethylaminocarbonylamino group, a difluoromethylaminocarbonylamino group, a trifluoroethylaminocarbonylamino group, a trichloroethylaminocarbonylamino group, a {trifluoromethyl(methyl) amino}carbonylamino group, a {difluoromethyl(methyl) amino}carbonylamino group, a {trifluoroethyl(methyl) amino}carbonylamino group, a {trichloroethyl(methyl) amino}carbonylamino group, a {trifluoromethyl(ethyl) amino}carbonylamino group, a {difluoromethyl(ethyl) amino}carbonylamino group, a {trifluoroethyl(ethyl) amino}carbonylamino group, a {trichloroethyl(ethyl) amino}carbonylamino group, a trifluoromethylaminocarbonyl(methyl)amino group, a difluoromethylaminocarbonyl(methyl)amino group, a trifluoroethylaminocarbonyl(methyl)amino group, a trichloroethylaminocarbonyl(methyl)amino group, a trifluoromethylaminocarbonyl(ethyl)amino group, a difluoromethylaminocarbonyl(ethyl)amino group, a trifluoroethylaminocarbonyl(ethyl)amino group, a trichloroethylaminocarbonyl(ethyl)amino group, a {trifluoromethyl(methyl) amino}carbonyl(methyl)amino group, a {difluoromethyl (methyl)amino}carbonyl(methyl)amino group, a {trifluoroethyl(methyl)amino}carbonyl(methyl)amino group, a {trichloroethyl(methyl)amino}carbonyl(methyl) amino group, a {trifluoromethyl(methyl)amino}carbonyl (ethyl)amino group, a {difluoromethyl(methyl) amino}carbonyl(ethyl)amino group, a {trifluoroethyl (methyl)amino}carbonyl(ethyl)amino group, a {trichloroethyl(methyl)amino}carbonyl(ethyl)amino group, a {trifluoromethyl(ethyl)amino}carbonyl(methyl)amino group, a {difluoromethyl(ethyl)amino}carbonyl(methyl) amino group, a {trifluoroethyl(ethyl)amino}carbonyl(methyl)amino group, a {trichloroethyl(ethyl)amino}carbonyl (methyl)amino group, a {trifluoromethyl(ethyl) amino}carbonyl(ethyl)amino group, a {difluoromethyl (ethyl)amino}carbonyl(ethyl)amino group, a {trifluoroethyl (ethyl)amino}carbonyl(ethyl)amino group, or a {trichloroethyl(ethyl)amino}carbonyl(ethyl)amino group;

an arylaminocarbonylamino group, such as a phenylaminocarbonylamino group, a {phenyl(methyl) amino}carbonylamino group, a {phenyl)ethyl) amino}carbonylamino group, a phenylaminocarbonyl (methyl)amino group, a phenylaminocarbonyl(ethyl)amino group, a {methyl(phenyl)amino}carbonyl(methyl)amino group, a {methyl(phenyl)amino}carbonyl(ethyl)amino group, an {ethyl(phenyl)amino}carbonyl(methyl)amino group, or an {ethyl(phenyl)amino}carbonyl(ethyl)amino group; an arylalkylaminocarbonylamino group, such as a benzylaminocarbonylamino group, a {benzyl(methyl) amino}carbonylamino group, a {benzyl(ethyl) amino}carbonylamino group, a benzylaminocarbonyl(methyl)amino group, a benzylaminocarbonyl(ethyl)amino group, a {methyl(benzyl)amino}carbonyl(methyl)amino group, a {methyl(benzyl)amino}carbonyl(ethyl)amino group, an {ethyl(benzyl)amino}carbonyl(methyl)amino group, or an {ethyl(benzyl)amino}carbonyl(ethyl)amino group; a cyclic aminocarbonylamino group, such as a pyrrolidinocarbonylamino group, a piperidinocarbonylamino group, a morpholinocarbonylamino group, a pyrrolidinocarbonyl(methyl)amino group, a piperidinocarbonyl(methyl) amino group, a morpholinocarbonyl(methyl)amino group, a pyrrolidinocarbonyl(ethyl)amino group, a piperidinocarbonyl(ethyl)amino group, or a morpholinocarbonyl(ethyl)amino group;

an alkylaminocarbonyl group, such as a methylaminocarbonyl group, an ethylaminocarbonyl group, a propylaminocarbonyl group, an isopropylaminocarbonyl group, a butylaminocarbonyl group, an isobutylaminocarbonyl group, a sec-butylaminocarbonyl group, a tert-butylaminocarbonyl group, a dimethylaminocarbonyl group, an {ethyl(methyl)amino}carbonyl group, a {methyl(propyl)amino}carbonyl group, an {isopropyl(methyl)amino}carbonyl group, a {butyl(methyl)amino}carbonyl group, an {isobutyl(methyl)amino}carbonyl group, a {sec-butyl(methyl)amino}carbonyl group, a {tert-butyl(methyl)amino}carbonyl group, an {ethyl(propyl)amino}carbonyl group, an {ethyl(isopropyl)amino}carbonyl group, a {butyl(ethyl)amino}carbonyl group, an {isobutyl(ethyl)amino}carbonyl group, a {sec-butyl(ethyl)amino}carbonyl group, or a {tert-butyl(ethyl)amino}carbonyl group; a cycloalkylaminocarbonyl group, such as a cyclopropylaminocarbonyl group, a cyclobutylaminocarbonyl group, a cyclopentylaminocarbonyl group, a cyclohexylaminocarbonyl group, a {cyclopropyl(methyl)amino}carbonyl group, a {cyclobutyl(methyl)amino}carbonyl group, a {cyclopentyl(methyl)amino}carbonyl group, a {cyclohexyl(methyl)amino}carbonyl group, a {cyclopropyl(ethyl)amino}carbonyl group, a {cyclobutyl(ethyl)amino}carbonyl group, a {cyclopentyl(ethyl)amino}carbonyl group, or a {cyclohexyl(ethyl)amino}carbonyl group; a halogen-substituted alkylaminocarbonyl group, such as a trifluoromethylaminocarbonyl group, a difluoromethylaminocarbonyl group, a trifluoroethylaminocarbonyl group, a trichloroethylaminocarbonyl group, a {trifluoromethyl(methyl)amino}carbonyl group, a {difluoromethyl(methyl)amino}carbonyl group, a {trifluoroethyl(methyl)amino}carbonyl group, a {trichloroethyl(methyl)amino}carbonyl group, a {trifluoromethyl(ethyl)amino}carbonyl group, a {difluoromethyl(ethyl)amino}carbonyl group, a {trifluoroethyl(ethyl)amino}carbonyl group, or a {trichloroethyl(ethyl)amino}carbonyl group; an arylaminocarbonyl group, such as a phenylaminocarbonyl group, a {phenyl(methyl)amino}carbonyl group, or a {phenyl(ethyl)amino}carbonyl group; an arylalkylaminocarbonyl group, such as a benzylaminocarbonyl group, a {benzyl(methyl)amino}carbonyl group or a {benzyl(ethyl)amino}carbonyl group; a cyclic aminocarbonyl group, such as a pyrrolidinocarbonyl group, a piperidinocarbonyl group or a morpholinocarbonyl group;

an alkoxycarbonyloxy group, such as a methoxycarbonyloxy group, an ethoxycarbonyloxy group, a propoxycarbonyloxy group, an isopropoxycarbonyloxy group, a butoxycarbonyloxy group, an isobutoxycarbonyloxy group, a sec-butoxycarbonyloxy group, or a tert-butoxycarbonyloxy group; a cycloalkoxycarbonyloxy group, such as a cyclopropoxycarbonyloxy group, a cyclobutoxycarbonyloxy group, a cyclopentyloxycarbonyloxy group, or a cyclohexyloxycarbonyloxy group; a halogen-substituted alkoxycarbonyloxy group, such as a trifluoromethoxycarbonyloxy group, a difluoromethoxycarbonyloxy group, a trifluoroethoxycarbonyloxy group or a trichloroethoxycarbonyloxy group; an aryloxycarbonyloxy group, such as a phenoxycarbonyloxy group; an arylalkyloxycarbonyloxy group, such as a benzyloxycarbonyloxy group; an alkylamino group, such as a methylamino group, an ethylamino group, a propylamino group, an isopropylamino group, a dimethylamino group, a diethylamino group, a dipropylamino group, or a diisopropylamino group; a cyclic amino group, such as a pyrrolidino group, a piperidino group, or a morpholino group; a silyloxy group, such as a tert-butyldimethylsilyloxy group, a tert-butyldiphenylsilyloxy group or a dimethylphenylsilyloxy group; a halogen atom, such as chlorine, fluorine, bromine or iodine; a nitro group; and a cyano group, or the like.

A substitution position of the substituent may be on an aryl moiety that constitutes the arylalkyl group or an alkyl moiety, and preferably on the aryl group.

When the arylalkyl group has a substituent on the aryl group, the number of the substituent is not particularly limited. When the arylalkyl group is substituted by two or more substituents, the substituents may be the same or composed of two or more kinds, without particularly being limited.

The aryl group in R1 and R2 in Formula (2) represents a phenyl group, a naphthyl group, an anthranyl group, a phenanthryl group, or the like.

The aryl group of the arylalkyl group in R1 and R2 in Formula (2) has the same definition as the aryl group in R1 and R2 as mentioned above.

The alkyl moiety of the arylalkyl group in R1 and R2 in Formula (2) is an alkylene group having 1 to 4 carbon atoms.

The acyl group in the acyl group having 1 to 6 carbon atoms which may be substituted in R1 and R2 in Formula (2), represents a formyl group, a methylcarbonyl group, an ethylcarbonyl group, a propylcarbonyl group, an isopropylcarbonyl group, a butylcarbonyl group, an isobutylcarbonyl group, a sec-butylcarbonyl group, a tert-butylcarbonyl group, a pentylcarbonyl group, an isoamylcarbonyl group, a 3-methyl-2-butylcarbonyl group, a tert-pentylcarbonyl group, a neo-pentylcarbonyl group, a 2-pentylcarbonyl group, a 3-pentylcarbonyl group, or the like.

R1 and R2 in Formula (2) may be together represent an atomic group that forms a 5- or 6-membered ring containing 0 or 1 hetero atom with the nitrogen atom to which R1 and R2 are bonded. Specific examples of the 5- or 6-membered ring structure include a pyrrolidino group, a piperidino group, and a morpholino group, or the like.

The alkyl group having 1 to 6 carbon atoms in R3 in Formula (2) has the same definition as the alkyl group having 1 to 6 carbon atoms in R1 and R2 in Formula (2).

The cycloalkyl group having 3 to 6 carbon atoms in R3 in Formula (2) has the same definition as the cycloalkyl group having 3 to 6 carbon atoms in R1 and R2 in Formula (2).

The aryl group which may be substituted in R3 in Formula (2) has the same definition as the aryl group which may be substituted in R1 and R2 in Formula (2).

The arylalkyl group which may be substituted in R3 in Formula (2) has the same definition as the arylalkyl group which may be substituted in R1 and R2 in Formula (2).

The alkyl group having 1 to 6 carbon atoms in R4 in Formula (2) has the same definition as the alkyl group having 1 to 6 carbon atoms in R1 and R2 in Formula (2).

The cycloalkyl group having 3 to 6 carbon atoms for R4 in Formula (2) has the same definition as the cycloalkyl group having 3 to 6 carbon atoms in R1 and R2 in Formula (2).

The aryl group which may be substituted in R4 in Formula (2) has the same definition as the aryl group which may be substituted in R1 and R2 in Formula (2).

The arylalkyl group which may be substituted in R4 in Formula (2) has the same definition as the arylalkyl group which may be substituted in R1 and R2 in Formula (2).

The use amount of the compound represented by Formula (2) is not particularly limited insofar as it is 1 equivalent or more to the compound represented by Formula (1). From an economical viewpoint, the amount of the compound represented by Formula (2) is preferably 1 equivalent or more and 2 equivalents or less to the compound represented by Formula (1).

The compound represented by Formula (2) may be commercially available products or may be produced with reference to method described in Japanese Patent Application Laid-Open Publication (JP-A) No. Hei 2-286652.

The compound represented by Formula (2) may be a compound having either a trans structure or a cis structure, or a compound including a trans isomer and a cis isomer mixed at an arbitrary ratio, and the structure thereof is not limited.

In the method for producing fluorine-containing acylacetic acid derivative in accordance with the present invention, the compound represented by Formula (2) is preferably a compound group wherein R1 and R2 each independently represent an alkyl group having 1 to 6 carbon atoms or a cycloalkyl group having 3 to 6 carbon atoms, or together represent an atomic group that forms a 5- or 6-membered ring containing 0 or 1 hetero atom with the nitrogen atom to which R1 and R2 are bonded, and R3 represents a hydrogen atom. Further, the compound represented by Formula (2) is more preferably a compound group wherein R1 and R2 each independently represent an alkyl group having 1 to 6 carbon atoms, R3 represents a hydrogen atom, and R4 represents an alkyl group having 1 to 6 carbon atoms. More preferably, the compound represented by Formula (2) is a compound group wherein R1 and R2 respectively represent a methyl group, R3 represents a hydrogen atom, and R4 represents a methyl group or an ethyl group.

In the present invention, at least one halogenating agent is used. In the following, the halogenating agent will be described in detail.

The halogenating agent may be selected from reagents which may substitute a hydroxy group of the compound represented by Formula (1) by a halogen atom. There is no particular limitation to the halogenating agent, insofar as the reaction proceeds.

Specific examples of the halogenating agent include sulfur-containing halogenating agents such as sulfuryl chloride, thionyl chloride, and thionyl bromide, carbonyl-containing halogenating agents such as oxalyl chloride, oxalyl bromide, and phosgene, and phosphorus-containing halogenating agents such as phosphorus oxychloride, phosphorus trichloride, phosphorus tribromide and phosphorus pentachloride.

The amount of the halogenating agent to be used is not particularly limited insofar as it is 1 equivalent or more to the compound represented by Formula (1). From an economical viewpoint, the amount of the halogenating agent is preferably 1 equivalent or more and 3 equivalents or less to the compound represented by Formula (1).

As the halogenating agent, oxalyl chloride and phosgene are preferable in the present invention.

The halogenating agent may also be used by converting to a Vilsmeier reagent by adding a formamide derivative, such as dimethylformamide.

There is no particular limitation to the amount of the formamide derivative to be used. From an economical viewpoint, the amount of the formamide derivative is 3 equivalents or less to the compound represented by Formula (1).

The Vilsmeier reagent is a salt containing a compound represented by the following Formula (7).

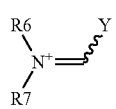

(7)

wherein R5 and R6 each independently represent an alkyl group having 1 to 6 carbon atoms and Y represents a halogen atom).

The alkyl group having 1 to 6 carbon atoms in R6 and R7 in Formula (7) has the same definition as the alkyl group having 1 to 6 carbon atoms in Rf in Formula (1).

The halogen atom in Y in Formula (7) is a fluorine atom, a chlorine atom, a bromine atom, or an iodine atom.

In the following, the compound represented by Formula (3) will be described in detail.

Rf in Formula (3) has the same definition as Rf in Formula (1). R1, R2, R3 and R4 in Formula (3) have the same definition as represents R1, R2, R3 and R4 in Formula (2).

The compound represented by Formula (3) may be a compound having either a trans structure or a cis structure, or a compound including a trans isomer and a cis isomer mixed at an arbitrary ratio, and the structure thereof is not limited.

In the method for producing a fluorine-containing acylacetic acid derivative represented by Formula (3) in accordance with the present invention, a solvent may be used if necessary.

Specific examples of the solvent include aprotic solvents, including halogen solvents, such as dichloromethane, chloroform, and 1,2-dichloroethane; aromatic solvents, such as benzene, toluene, xylene, and anisole; hydrocarbon solvents, such as hexane, and heptane; ester solvents, such as ethyl acetate, butyl acetate, and isopropyl acetate; ether solvents, such as diethyl ether, diisopropyl ether, 1,2-dimethoxyethane, tetrahydrofuran, and dioxane; nitrile solvents, such as acetonitrile and propionitrile; and ketone solvents such as methyl isobutyl ketone.

The amount of the solvent to be use is not particularly limited, but is usually preferably 3 times ore more and 40 times or less the weight of the compound represented by Formula (2).

The reaction temperature is not particularly limited insofar as it is adjusted so that each of the compounds does not decompose, but is usually from −30° C. to 150° C. or not more than the boiling point of the solvent.

Regarding the method for charging a reagent in the method for producing a fluorine-containing acylacetic acid derivative in accordance with the present invention, the halogenating agent is charged into a mixture containing the compound represented by Formula (1), the compound represented by Formula (2), and a base, at the last stage.

If necessary, a formamide derivative may be optionally added to the mixture containing the compound represented by Formula (1), the compound represented by Formula (2), and a base.

The addition of halogenating agent to the mixture is an important feature of the present invention, and thereby the yield of the compound represented by Formula (3) may be remarkably improved.

In the following, a post-treatment process will be described.

A reaction mixture containing the compound represented by Formula (3) that has been obtained by reacting the compound represented by Formula (1) with the compound represented by Formula (2) may be washed with water, an aqueous alkali solution, an aqueous acid solution, or a saline solution.

The aqueous alkali solution or aqueous acid solution for use in the washing is not particularly limited insofar as it does not decompose the compound represented by Formula (3). In general, examples of the aqueous alkali solution include an aqueous sodium hydrogen carbonate solution, an aqueous sodium carbonate solution, an aqueous sodium hydroxide solution, an aqueous potassium hydrogen carbonate solution, an aqueous potassium carbonate solution, and an aqueous potassium hydroxide solution; and examples of the aqueous acid solution include an aqueous hydrochloric acid solution and an aqueous sulfuric acid solution.

The number of washing of the reaction mixture is not particularly limited.

The reaction mixture containing the compound represented by Formula (3) which has been washed with water, an aqueous alkali solution, or an aqueous acid solution may be subjected to dehydration with sodium sulfate, magnesium sulfate, or the like.

The reaction mixture containing the compound represented by Formula (3) which has been washed with water, an aqueous alkali solution, an aqueous acid solution, or a saline solution; or the reaction mixture which has been dehydrated with sodium sulfate, magnesium sulfate, or the like may be used directly without further processing, for example, in conversion into pyrazole. Alternatively, such a reaction mixture may be used after distillation of the solvent. Alternatively, such a reaction mixture may be used after purification thereof by recrystallization, reprecipitation, washing with solvent, distillation, or the like.

The solvent for use in the recrystallization, reprecipitation, or washing with solvent is not particularly limited, insofar as it does not decompose the compound represented by Formula (3).

Specific examples of the solvent for use in the recrystallization, reprecipitation, or washing with solvent include water; halogen solvents, such as dichloromethane, chloroform, and 1,2-dichloroethane; aromatic solvents, such as benzene, toluene, xylene, and anisole; ether solvents, such as diethyl ether, diisopropyl ether, and 1,2-dimethoxyethane; alcohol solvents, such as methanol, ethanol, and isopropyl alcohol; hydrocarbon solvents, such as heptane, hexane, and cyclohexane; ester solvents, such as ethyl acetate, isopropyl acetate, and butyl acetate; nitrile solvents, such as acetonitrile, and propionitrile; and ketone solvents such as methyl isobutyl ketone. These solvents may be used singularly or in a mixture of two or more kinds thereof at an arbitrary ratio.

The amount of the solvent to be used is not particularly limited insofar as it is determined according to a desired level of yield or purity. In general, the weight of the solvent is preferably 1 times or more and 40 times or less the weight of the compound represented by Formula (3).

The method for producing the compound represented by Formula (3) in accordance with the present invention may be preferably applied to a compound group of the compound represented by Formula (2), wherein R1 and R2 each independently represent an alkyl group having 1 to 6 carbon atoms or a cycloalkyl group having 3 to 6 carbon atoms, or together represent an atomic group that forms a 5- or 6-membered ring containing 0 or 1 hetero atom with the nitrogen atom to which R1 and R2 are bonded, and R3 represents a hydrogen atom. Further, this method can be preferably applied to a compound group wherein R1 and R2 each independently represent an alkyl group having 1 to 6 carbon atoms, R3 represents hydrogen, and R4 represents an alkyl group having 1 to 6 carbon atoms. Further, this method can be preferably applied to a compound group of Formula (1) wherein Rf represents a trifluoromethyl group or a difluoromethyl group, R1 and R2 respectively represent a methyl group, R3 represents a hydrogen atom, and R4 represents a methyl group or an ethyl group.

The method for producing the compound represented by Formula (3) in accordance with the present invention is characterized in that the fluorine-containing alkyl carboxylic acid derivative represented by Formula (1) which is convenient to handle may be used as a starting material. Thereby, it is possible to provide a production method of the compound represented by Formula (3) which is convenient and feasible on an industrial scale.

The method for producing a fluorine-containing pyrazole-carboxylic acid ester derivative represented by the following Formula (5) in accordance with the present invention comprises a process of reacting a compound represented by the following Formula (3) with a compound represented by the following Formula (4), and other processes such as a post-treatment process, if necessary.

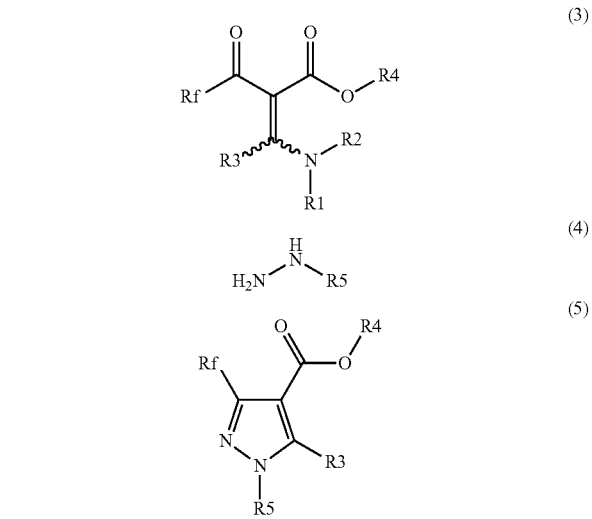

In Formulae, Rf represents an alkyl group having 1 to 6 carbon atoms which is substituted by at least one fluorine atom. R1 and R2 each independently represent a hydrogen atom, an alkyl group having 1 to 6 carbon atoms, a cycloalkyl group having 3 to 6 carbon atoms, an aryl group which may be substituted, an arylalkyl group which may be substituted, or an acyl group having 1 to 6. carbon atoms which may be substituted, or together represent an atomic group that forms a 5- or 6-membered ring containing 0 or 1 hetero atom with the nitrogen atom to which R1 and R2 are bonded. R3 represents a hydrogen atom, an alkyl group having 1 to 6 carbon atoms, a cycloalkyl group having 3 to 6 carbon atoms, an aryl group which may be substituted, or an arylalkyl group which may be substituted. R4 represents an alkyl group having 1 to 6 carbon atoms, a cycloalkyl group having 3 to 6 carbon atoms, an aryl group which may be substituted, or an arylalkyl group which may be substituted. R5 represents an alkyl group having 1 to 6 carbon atoms, a cycloalkyl group having 3 to 6 carbon atoms, an aryl group which may be substituted, or an arylalkyl group which may be substituted.

In the following, the compound represented by Formula (4) will be described in detail.

The alkyl group having 1 to 6 carbon atoms in R5 in Formula (4) has the same definition as the alkyl group having 1 to 6 carbon atoms in Rf in Formula (1).

The cycloalkyl group having 3 to 6 carbon atoms for R5 in Formula (4) has the same definition as the cycloalkyl group having 3 to 6 carbon atoms in R1 and R2 in Formula (2).

The aryl group which may be substituted for R5 in Formula (4) has the same definition as the aryl group which may be substituted in R1 and R2 in Formula (2).

The arylalkyl group which may be substituted in R5 in Formula (4) has the same definition as the arylalkyl group which may be substituted in R1 and R2 in Formula (2).

The use amount of the compound represented by Formula (4) in the present invention is not particularly limited insofar as it is 0.9 equivalents or more with respect to the compound represented by Formula (3). From an economical viewpoint, however, the amount of the compound represented by Formula (4) may be 0.9 equivalents or more and 3 equivalents or less with respect to the compound represented by Formula (3).

The compound represented by Formula (4) may be commercially available products or may be produced by known methods.

The method for producing the compound represented by Formula (4) in accordance with the present invention may be preferably applied to a compound group wherein R5 represents an alkyl group having 1 to 6 carbon atoms. Further, this method may be preferably applied to a compound wherein R5 represents a methyl group.

In the following, Formula (5) will be described in detail.

Rf in Formula (5) has the same definition as Rf in Formula (1).

R3, R4 and R5 in Formula (5) have the same definition as represents R3, R4 and R5 in Formula (2).

The process of reacting the compound represented by Formula (3) with the compound represented by Formula (4) may be any one of a method for charging the compound represented by Formula (3) into the compound represented by Formula (4), or a method for charging the compound represented by Formula (4) into the compound represented by Formula (3). The charging type may be powder charging, dropwise addition, or the like. Here, the compound represented by Formula (3) or Formula (4) may be dissolved or suspended in an appropriate solvent prior to use.

A solvent may be used in this reaction. There is no particular limitation to the solvent to be used, insofar as the reaction proceeds. Specific examples of the solvent for use include halogen solvents, such as dichloromethane, chloroform, and 1,2-dichloroethane; aromatic solvents, such as benzene, toluene, xylene, and anisole; ether solvents, such as diethyl ether, diisopropyl ether, 1,2-dimethoxyethane, tetrahydrofuran, and dioxane; hydrocarbon solvents, such as heptane, hexane, and cyclohexane; ester solvents, such as ethyl acetate, isopropyl acetate, and butyl acetate; amide solvents such as N-methyl-2-pyrrolidone, N,N-dimethylformamide, and N,N-dimethylacetamide; urea solvents such as 1,3-dimethyl-2-imidazolidinone, 1,3-dimethyl-3,4,5,6-tetrahydro-2(1H)-pyrimidinone; sulfonyl oxide solvents such as dimethyl sulfoxide; ketone solvents such as methyl isobutyl ketone; and water. These solvents may be used singularly or in a mixture of two or more kinds thereof at an arbitrary ratio.

The amount of the solvent to be used is not particularly limited. In general, the weight of the solvent is preferably 3 times or more and 40 times or less the weight of the compound represented by Formula (3).

The reaction temperature is not particularly limited insofar as the desired reaction proceeds, but is usually from −40° C. to 150° C. or not more than the boiling point of the solvent.

The post-treatment of the reaction mixture containing the compound represented by Formula (5) may be carried out without particular limitation insofar as the compound represented by Formula (5) does not decompose. In the following, specific examples of the post-treatment method will be described.

With respect to a reaction mixture where a bilayer system solvent consisting of a water-incompatible organic solvent and water is a reaction solvent, the organic layer containing the compound represented by Formula (5) may be obtained by liquid separation.

With respect to a reaction mixture where a single system solvent consisting of a water-compatible organic solvent and water is a reaction solvent, an organic solvent is distilled off under reduced pressure, and the compound represented by Formula (5) may be then extracted by the organic solvent which was separated from water.

With respect to a reaction mixture where a water-incompatible organic solvent is a reaction solvent, the compound represented by Formula (5) may be obtained directly by distillation of the solvent under reduced pressure. Before the solvent distillation, a liquid separation operation to be described hereinafter may be carried out.

With respect to a reaction mixture where a water-compatible organic solvent is a reaction solvent, the compound represented by Formula (5) may be obtained directly by distillation of the solvent under reduced pressure. After the solvent distillation, a liquid separation operation to be described hereinafter may be carried out by adding water to the organic solvent separated from water.

With respect to a reaction mixture where water is a reaction solvent, when the compound represented by Formula (5) is precipitated, the resulting precipitate may be collected by filtration. When the corresponding compound is not precipitated, extraction may be carried out by adding the organic solvent separated from water.

The organic layer containing the compound represented by Formula (5) may be washed with water, an aqueous acid solution, an aqueous alkali solution, or a saline solution. There is no particular limitation to the washing frequency, washing sequence, and the like insofar as the compound does not decompose.

The aqueous acid solution or aqueous alkali solution for use in the washing is not particularly limited insofar as it does not decompose the compound represented by Formula (5). In general, examples of the aqueous acid solution include an aqueous hydrochloric acid solution and an aqueous sulfuric acid solution; and examples of the aqueous alkali solution include an aqueous sodium hydrogen carbonate solution, an aqueous sodium carbonate solution, an aqueous sodium hydroxide solution, an aqueous potassium hydrogen carbonate solution, an aqueous potassium carbonate solution, and an aqueous potassium hydroxide solution.

The organic layer containing the compound represented by Formula (5) may be subjected to dehydration with sodium sulfate, magnesium sulfate, or the like.

The organic layer containing the compound represented by Formula (5) may be used directly without further processing, for example, in a hydrolysis process. Alternatively, the compound may be subjected to hydrolysis after distillation of the solvent under reduced pressure.

In order to improve purity of the compound represented by Formula (5), distillation, recrystallization, reprecipitation, washing with solvent, or the like may be carried out.

The solvent for use in the recrystallization, reprecipitation, or washing with solvent is not particularly limited, insofar as it does not decompose the compound represented by Formula (5).

Specific examples of the solvent for use in the recrystallization, reprecipitation, or washing with solvent include halogen solvents, such as dichloromethane, chloroform, and 1,2-dichloroethane; aromatic solvents, such as benzene, toluene, xylene, and anisole; ether solvents, such as diethyl ether, diisopropyl ether, 1,2-dimethoxyethane, tetrahydrofuran, and dioxane; alcohol solvents, such as methanol, ethanol, and isopropyl alcohol; hydrocarbon solvents, such as heptane, hexane, and cyclohexane; ester solvents, such as ethyl acetate, isopropyl acetate, and butyl acetate; nitrile solvents, such as acetonitrile, and propionitrile; ketone solvents such as methyl isobutyl ketone; and water. These solvents may be used singularly or in a mixture of two or more kinds thereof at an arbitrary ratio.

The amount of the solvent to be used is not particularly limited insofar as it is determined according to a desired level of yield or purity. In general, the weight of the solvent is preferably 1 times or more and 40 times or less the weight of the compound represented by Formula (5).

The method for producing the compound represented by Formula (5) in accordance with the present invention may be preferably applied to a compound group wherein R1 and R2 each independently represent an alkyl group having 1 to 6 carbon atoms, or a cycloalkyl group having 3 to 6 carbon atoms, or together represent an atomic group that forms a 5- or 6-membered ring containing 0 or 1 hetero atom with the nitrogen atom to which R1 and R2 are bonded, and R3 represents a hydrogen atom. Further, this method may be preferably applied to a compound group wherein R1 and R2 each independently represent an alkyl group having 1 to 6 carbon atoms, R3 represents a hydrogen atom, R4 represents an alkyl group having 1 to 6 carbon atoms, and R5 represents an alkyl group having 1 to 6 carbon atoms. Further, this method may be preferably applied to a compound group wherein Rf represents a trifluoromethyl group or a difluoromethyl group, R1 and R2 respectively represent a methyl group, R3 represents a hydrogen atom, R4 represents a methyl group or an ethyl group, and R5 represents a methyl group.

The method for producing the fluorine-containing pyrazolecarboxylic acid ester derivative represented by Formula (5) in accordance with the present invention is characterized by reacting the compound represented by Formula (3) prepared according to the above-mentioned method for producing a fluorine-containing acylacetic acid derivative represented by Formula (3) with the compound represented by Formula (4). Thereby, it is possible to provide a production method of the compound represented by Formula (5) which is feasible in a convenient manner with a high yield on an industrial scale.

The method for producing a fluorine-containing pyrazolecarboxylic acid derivative represented by the following Formula (6) in accordance with the present invention includes a process of hydrolyzing the compound represented by the following Formula (5). Further, this method may include other processes such as a post-treatment process, if necessary.

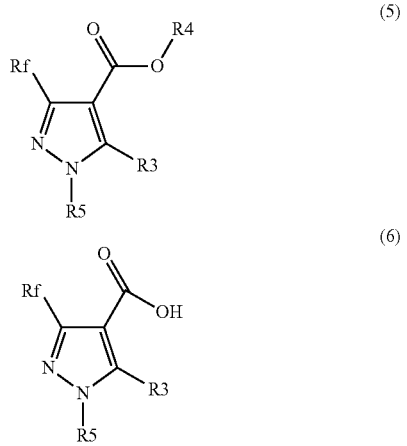

In Formulae, Rf represents an alkyl group having 1 to 6 carbon atoms which is substituted by at least one fluorine atom. R3 represents a hydrogen atom, an alkyl group having 1 to 6 carbon atoms, a cycloalkyl group having 3 to 6 carbon atoms, an aryl group which may be substituted, or an arylalkyl group which may be substituted. R4 represents an alkyl group having 1 to 6 carbon atoms, a cycloalkyl group having 3 to 6 carbon atoms, an aryl group which may be substituted, or an arylalkyl group which may be substituted. R5 represents, an alkyl group having 1 to 6 carbon atoms, a cycloalkyl group having 3 to 6 carbon atoms, an aryl group which may be substituted, or an arylalkyl group which may be substituted.

In the following, the compound represented by Formula (6) will be described in detail.

Rf in Formula (6) has the same definition as Rf in Formula (1).

R3 and R5 in Formula (6) have the same definition as represents R3 and R5 in Formula (2).

In the hydrolysis process of the compound represented by Formula (5) in the present invention, at least water is reacted with the compound represented by Formula (5), but, it is preferred to use an acid or a base, in addition to water.

First, the hydrolysis reaction will be described in which the compound represented by Formula (5) and water are reacted under acidic conditions, and the reaction product is converted into the compound represented by Formula (6).

The amount of water to be used is not particularly limited insofar as it is 1 equivalent or more with respect to the compound represented by Formula (5). Further, water may be used as a solvent. There is no particular limitation to the amount of the solvent, insofar as the above-specified equivalent number is satisfied. In general, the upper limit thereof may be 40 times or less the weight of the compound represented by Formula (5).

The acid to be used is not particularly limited insofar as the reaction proceeds, and is an organic or inorganic acid.

Specific examples of the organic acid include sulfonic acids such as methane sulfonic acid and toluene sulfonic acid, carboxylic acids such as trichloroacetic acid and trifluoroacetic acid, and the like.

Specific examples of the inorganic acid include hydrochloric acid, hydrobromic acid, sulfuric acid, and the like.

The amount of the acid to be used is not particularly limited insofar as the desired reaction proceeds. In general, the amount of the acid is 0.1 equivalents or more with respect to the compound represented by Formula (5).

In the present invention, a solvent may be used, if necessary. Examples of the solvent include carboxylic acid solvents such as acetic acid; alcohol solvents, such as methanol, ethanol, propanol, isopropyl alcohol, and butanol; ether solvents, such as tetrahydrofuran, and dioxane; and water. These solvents may be used singularly or in a mixture of two or more kinds thereof at an arbitrary ratio.

The amount of the solvent to be used is not particularly limited. In general, the weight of the solvent is preferably 3 times or more and 40 times or less the weight of the compound represented by Formula (5).

The reaction temperature is not particularly limited insofar as the desired reaction proceeds, but is usually from 0° C. to 150° C. or not more than the boiling point of the solvent.

There is no particular limitation to the post-treatment method of the reaction mixture containing the compound represented by Formula (6) obtained under the acidic conditions may be carried out without particular limitation insofar as the desired product, i.e., the compound represented by Formula (6) does not decompose. In the following, specific examples of the post-treatment method will be described.

When the compound represented by Formula (6) is precipitated from the reaction mixture or the solvent-distilled reaction mixture, the resulting precipitate is collected by filtration.

The reaction mixture or the solvent-distilled reaction mixture may be subjected to liquid separation. Here, if necessary, water or an organic solvent may be added. Water for use in liquid separation may contain a salt such as sodium chloride. There is no particular limitation to the frequency of liquid separation.

Specific examples of the organic solvent include halogen solvents, such as dichloromethane, chloroform, and 1,2-dichloroethane; aromatic solvents, such as benzene, toluene, xylene, and anisole; ether solvents, such as diethyl ether, and diisopropyl ether; hydrocarbon solvents, such as heptane, hexane, and cyclohexane; and ester solvents, such as ethyl acetate, isopropyl acetate, and butyl acetate. These solvents may be used singularly or in a mixture of two or more kinds thereof at an arbitrary ratio.

The amount of the organic solvent to be used is not particularly limited. In general, the weight of the organic solvent is preferably 1 times ore more and 40 times or less the weight of the compound represented by Formula (6).

The organic layer containing the compound represented by Formula (6) obtained by liquid separation may be subjected to dehydration with sodium sulfate, magnesium sulfate, or the like.

The organic layer containing the compound represented by Formula (6) obtained by liquid separation, or the organic layer subjected to dehydration with sodium sulfate, magnesium sulfate, or the like is subjected to solvent distillation under reduced pressure, and the desired compound can be obtained.

Further, depending on the desired purity, the obtained compound may be further purified by recrystallization, reprecipitation, washing with solvent, distillation, or the like.

The solvent for use in the recrystallization, reprecipitation, or washing with solvent is not particularly limited, insofar as it does not decompose the compound represented by Formula (6).

Specific examples of the solvent for use in the recrystallization, reprecipitation, or washing with solvent include halogen solvents, such as dichloromethane, chloroform, and 1,2-dichloroethane; aromatic solvents, such as benzene, toluene, xylene, and anisole; ether solvents, such as diethyl ether, diisopropyl ether, 1,2-dimethoxyethane, tetrahydrofuran, and dioxane; alcohol solvents, such as methanol, ethanol, and isopropyl alcohol; hydrocarbon solvents, such as heptane, hexane, and cyclohexane; ester solvents, such as ethyl acetate, isopropyl acetate, and butyl acetate; nitrile solvents, such as acetonitrile, and propionitrile; and water. These solvents may be used singularly or in a mixture of two or more kinds thereof at an arbitrary ratio.

The amount of the solvent to be used is not particularly limited insofar as it is determined according to a desired level of yield or purity. In general, the weight of the solvent is preferably 1 times or more and 40 times or less the weight of the compound represented by Formula (6).

Next, the hydrolysis reaction will be described in which the compound represented by Formula (5) is reacted with water under alkaline conditions and is converted into the compound represented by Formula (6).

The amount of water to be used is not particularly limited insofar as it is 1 equivalent or more with respect to the compound represented by Formula (5). Further, water may be used as a solvent. There is no particular limitation to the amount of the solvent, insofar as the above-specified equivalent number is satisfied. In general, the upper limit thereof may be 40 times or less the weight of the compound represented by Formula (5).

The base to be used is not particularly limited insofar as the reaction proceeds, and is an organic or inorganic base.

Specific examples of the organic base include metal alkoxides such as sodium methoxide and sodium ethoxide, secondary amines such as diisopropyl amine, tertiary amines, such as triethylamine, tributylamine, trioctylamine, diisopropylethylamine, 1,4-diazabicyclo[2.2.2]octane, and 1,8-diazabicyclo[5.4.0]-7-undecene, and aromatic amines, such as pyridine, collidine, lutidine, and 4-dimethylaminopyridine.

Specific examples of the inorganic base include lithium hydroxide, sodium hydroxide, potassium hydroxide, sodium hydrogen carbonate, potassium hydrogen carbonate, sodium carbonate, and potassium carbonate.

These bases may be used singularly or in a mixture of two or more kinds at an arbitrary ratio.

The amount of the base to be used is not particularly limited insofar as the desired reaction proceeds. In general, the amount of the acid may be 1 equivalent or more and 20 equivalents or less with respect to the compound represented by Formula (5).

If necessary, a solvent may be used in the reaction. Examples of the solvent include alcohol solvents, such as methanol, ethanol, propanol, isopropyl alcohol, and butanol; ether solvents, such as tetrahydrofuran, and dioxane; and water. These solvents may be used singularly or in a mixture of two or more kinds thereof at an arbitrary ratio.

The amount of the solvent to be used is not particularly limited. In general, the weight of the solvent is preferably 3 times or more and 40 times or less the weight of the compound represented by Formula (5).

The reaction temperature is not particularly limited insofar as the desired reaction proceeds, but is usually from 0° C. to 150° C. or not more than the boiling point of the solvent.

There is no particular limitation to the post-treatment method of the reaction mixture containing the compound represented by Formula (6) obtained under the alkaline conditions insofar as the desired product, i.e., the compound represented by Formula (6) does not decompose. In the following, specific examples of the post-treatment method will be described.

The compound represented by Formula (6) prepared under the alkaline conditions is in the form of a salt in the reaction mixture. When the salt is precipitated in the reaction mixture, the resulting precipitate may be collected by filtration. On the other hand, when the salt is not precipitated, impurities may be removed by liquid separation with addition of an organic solvent separable from water. Before the liquid separation operation, the solvent may be removed by distillation under reduced pressure, or water or an aqueous solution containing sodium chloride may be added.

By adding an acid to the salt collected by filtration, the salt contained in reaction mixture purified by liquid separation, or the salt contained in the untreated reaction mixture, the corresponding salt may be converted into the compound represented by Formula (6).

Examples of the acid include organic acids such as methane sulfonic acid, and sulfonic acid, and inorganic acids such as hydrochloric acid, hydrobromic acid, and sulfuric acid.

The amount of acid to be used is not particularly limited insofar as it is at least 1 equivalent with respect to the base used in the reaction.

With respect to a method of obtaining the compound represented by Formula (6) prepared by acid addition, when the compound is precipitated from the reaction mixture, the resulting precipitate is collected by filtration. Further, irrespective of precipitation, the compound may also be extracted with an organic solvent. The compound may be obtained by subjecting the extracted organic layer to solvent distillation under reduced pressure. Before distillation under reduced pressure, dehydration may be carried out with sodium sulfate, magnesium sulfate, or the like.

Depending on the desired purity, the obtained compound may be further purified by recrystallization, reprecipitation, washing with solvent, distillation, or the like.

The solvent for use in the recrystallization, reprecipitation, or washing with solvent is not particularly limited, insofar as the compound represented by Formula (6) is not decomposed.

Specific examples of the solvent for use in the recrystallization, reprecipitation, or washing with solvent include water; halogen solvents, such as dichloromethane, chloroform, and 1,2-dichloroethane; aromatic solvents, such as benzene, toluene, xylene, and anisole; ether solvents, such as diethyl ether, diisopropyl ether, 1,2-dimethoxyethane, tetrahydrofuran, and dioxane; alcohol solvents, such as methanol, ethanol, and isopropyl alcohol; hydrocarbon solvents, such as heptane, hexane, and cyclohexane; ester solvents, such as ethyl acetate, isopropyl acetate, and butyl acetate; and nitrile solvents, such as acetonitrile, and propionitrile. These solvents may be used singularly or in a mixture of two or more kinds thereof at an arbitrary ratio.

The amount of the solvent to be used is not particularly limited insofar as it is determined according to a desired level of yield or purity. In general, the weight of the solvent is preferably 1 times ore more and 40 times or less the weight of the compound represented by Formula (6).

The method for producing the compound represented by Formula (6) in accordance with the present invention may be preferably applied to a compound group wherein R1 and R2 each independently represent an alkyl group having 1 to 6 carbon atoms, or a cycloalkyl group having 3 to 6 carbon atoms, or together represent an atomic group that forms a 5- or 6-membered ring containing 0 or 1 hetero atom with the nitrogen atom to which R1 and R2 are bonded, and R3 represents a hydrogen atom. This method may be preferably applied to a compound group wherein R1 and R2 each independently represent an alkyl group having 1 to 6 carbon atoms, R3 represents a hydrogen atom, R4 represents an alkyl group having 1 to 6 carbon atoms, and R5 represents an alkyl group having 1 to 6 carbon atoms. Further, this method may be preferably applied to a compound group wherein Rf represents a trifluoromethyl group or a difluoromethyl group, R1 and R2 respectively represent a methyl group, R3 represents a hydrogen group, R4 represents a methyl group or an ethyl group, and R5 represents a methyl group.

The method for producing the fluorine-containing pyrazolecarboxylic acid derivative represented by Formula (6) in accordance with the present invention is characterized by including a process of hydrolyzing the compound represented by the following Formula (5) prepared according to the above-mentioned method for producing a fluorine-containing pyrazolecarboxylic acid ester derivative in accordance with the present invention. Thereby, it is possible to conveniently produce the compound represented by Formula (6) on an industrial scale.

According to the foregoing description, it has become possible to provide a method for producing a fluorine-containing acylacetic acid derivative using a fluorine-containing alkyl carboxylic acid derivative, and methods for producing a fluorine-containing pyrazolecarboxylic acid ester derivative and a fluorine-containing pyrazolecarboxylic acid derivative, using the fluorine-containing acylacetic acid derivative.

EXAMPLES

In the following, the present invention will be described in more detail with reference to examples, but the present invention is not limited thereto. Hereinafter, ethyl 3-(dimethylamino) acrylate is referred to as Compound (I), ethyl 3-dimethylamino-2-trifluoroacetyl acrylate is referred to as Compound (II), ethyl 1-methyl-3-(trifluoromethyl)-1H-pyrazole-4-carboxylate is referred to as Compound (III), 1-methyl-3-(trifluoromethyl)-1H-pyrazole-4-carboxylic acid is referred to as Compound (IV), and a high-speed liquid chromatography is referred to as HPLC.

Example 1

Synthesis of Compound (II) Using Oxalylchloride as a Halogenating Agent

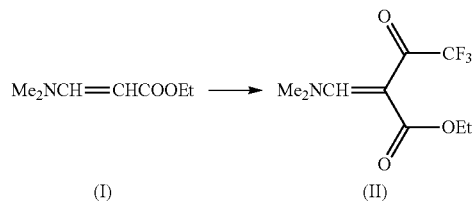

75 ml of toluene containing 6.28 g of Compound (I) and 8.87 g of triethylamine was cooled with ice, and 5.0 g of trifluoroacetic acid was added dropwise thereto. The mixture was stirred for 15 minutes under ice cooling, and 25 ml of toluene containing 5.58 g of oxalylchloride was added dropwise thereto. After continuing stirred for 2 hours at the same temperature, the reaction mixture was observed by HPLC, and the result showed that the reaction yield of Compound (II) was 83%.

Then, water was added to the reaction mixture for liquid separation. The separated organic layer was washed with saturated sodium bicarbonate solution, and then dried over sodium sulfate. After removal of sodium sulfate, the filtrate was concentrated under reduced pressure, and hexane was added to the residue, followed by stirring. The precipitate was filtered to afford 7.64 g (yield: 78%) of Compound (II) as a light tan solid.

<Material Data of Compound (II)>
$^1$H NMR(CDCl$_3$)δ1.31(3H, t, J=7.1 Hz), 2.90 (3H, s), 3.33 (3H, s), 4.22 (2H, q, J=7.1 Hz), 7.69 (1H, s).

Comparative Example 1

Synthesis of Compound (II) where Compound (I) was Charged at the Last Stage

Under ice cooling, 25 ml of toluene containing 5.57 g of oxalylchloride was added dropwise to 50 ml of toluene containing 5.0 g of trifluoroacetic acid. The mixture was stirred for 15 minutes at the same temperature, and 8.87 g of triethylamine was carefully added dropwise thereto. After stirring for another 1.5 hours at the same temperature, 25 ml of toluene containing 6.28 g of Compound (I) was added dropwise thereto, followed by stirring for 2 hours. The reaction mixture was observed by HPLC, and the result showed that the reaction yield of Compound (II) was only 23%.

Comparative Example 2

Synthesis of Compound (II) where Trifluoroacetic Acid was Charged at the Last Stage Under ice cooling, 25 ml of toluene containing 5.57 g of oxalylchloride was added dropwise to 50 ml of toluene containing 8.87 g of triethylamine and 6.28 g of Compound (I). Then, 25 ml of toluene containing 5.0 g of trifluoroacetic acid was added dropwise thereto, followed by stirring for 2 hours under ice cooling. The reaction mixture was observed by HPLC, and the result showed that the reaction yield of Compound (II) was trace.

Comparative Example 3

Synthesis of Compound (II) where Triethylamine was Charged at the Last Stage Under ice cooling, 25 ml of toluene containing 5.57 g of oxalylchloride was added dropwise to 50 ml of toluene containing 5.0 g of trifluoroacetic acid and 6.28 g of Compound (I). Then, 25 ml of toluene containing 8.87 g of triethylamine was added dropwise thereto, followed by stirring for 2 hours under ice cooling. The reaction mixture was observed by HPLC, and the result showed that the reaction yield of Compound (II) was only 9%.

From these results, it was found that a fluorine-containing acylacetic acid ester derivative can be conveniently and efficiently produced by adding a halogenating agent to a mixture containing a base, a fluorine-containing alkyl carboxylic acid and an acrylic ester derivative.

Example 2

Synthesis of Compound (II) Using Phosgene as a Halogenating Agent

To 65 g of toluene containing 6.28 g of Compound (I) and 8.87 g of triethylamine was cooled with ice, 5.00 g of trifluoroacetic acid was added dropwise.

Subsequently, 10.0 g of phosgene was allowed to pass through the reaction mixture, the temperature of the resultant was allowed to increase to room temperature from ice cooling, followed by stirring for 2 hours. Nitrogen was then allowed to pass through the reaction mixture for 1.5 hours.

Then, water was added to the reaction mixture for liquid separation. The separated organic layer was washed with saturated sodium bicarbonate solution, and then dried over sodium sulfate, followed by filtration. The filtrate was concentrated under reduced pressure, and hexane was added to the residue, followed by sufficient stirring. The precipitate was filtered to afford 8.89 g (yield: 85%) of Compound (II) as a light yellow solid.

Example 3

Synthesis of Compound (III)

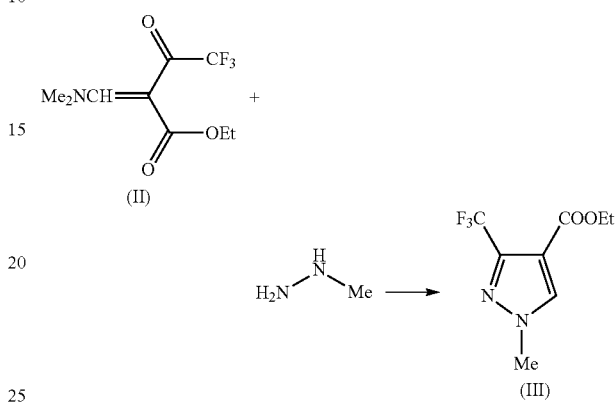

Under ice cooling, 50 ml of toluene containing 5.00 g of Compound (II) obtained in Example 2 dissolved therein, was added dropwise to 10 ml of water containing 1.18 g of methyl hydrazine. After stirring for 2 hours, the organic layer was separated, followed by liquid separation with 0.5 mol/L hydrochloric acid and then with a saturated sodium bicarbonate solution. The organic layer was dried over magnesium sulfate, followed by filtration. The filtrate was concentrated under reduced pressure. Hexane was added to the residue, followed by stirring. The precipitate was filtered to afford 3.36 g (yield: 72%) of Compound (III) as a white solid.

<Material Data of Compound (III)>

$^1$H NMR(CDCl$_3$)δ1.35(3H, t, J=7.3 Hz), 3.97(3H, s), 4.32 (2H, q, J=7.3 Hz), 7.92(1H, s).

Example 4

Synthesis of Compound (IV)

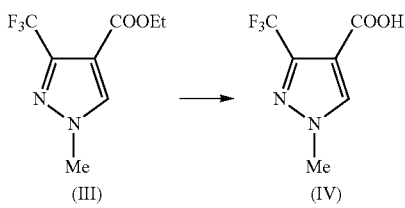

3.18 g of Compound (III) obtained by the method of Example 3 was added to 20 ml of water containing 1.15 g of sodium hydroxide dissolved therein, followed by heating to 60° C. The mixture was stirred for 2 hours, and then cooled to room temperature. Then, concentrated hydrochloric acid was added to achieve pH 1, followed by stirring for another 1 hour. The precipitate was filtered to afford 2.51 g (yield: 90%) of Compound (IV) as a white solid.

<Material Data of Compound (IV)>

$^1$H NMR(DMSO-d$_6$) δ3.93(3 H, s), 8.45(1 H, s).

Industrial Applicability

The present invention enables a method for producing a fluorine-containing acylacetic acid derivative and a method for producing a fluorine-containing pyrazole derivative using the fluorine-containing acylacetic acid derivative. The present methods are also suitable as an industrial production method due to convenience of operation while not using reagents which may cause problems upon mass production. Further, the fluorine-containing pyrazole derivative derived from the fluorine-containing acylacetic acid derivative can serve as an important raw material of agricultural/horticultural germicides and the like. Respectively, the present invention is industrially advantageous and thus has a great deal of potential in pharmaceuticals and agrochemical fields.

What is claimed is:

1. A method for producing a fluorine-containing acylacetic acid derivative represented by the following Formula (3), comprising obtaining a mixture containing a base, a compound represented by the following Formula (1), and a compound represented by the following Formula (2), and adding a halogenating agent to the mixture:

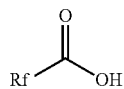
(1)

wherein Rf represents an alkyl group having 1 to 6 carbon atoms which is substituted by at least one fluorine atom;

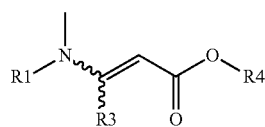
(2)

wherein R1 and R2 each independently represent a hydrogen atom, an alkyl group having 1 to 6 carbon atoms, a cycloalkyl group having 3 to 6 carbon atoms, an aryl group which may be substituted, an arylalkyl group which may be substituted, or an acyl group having 1 to 6 carbon atoms which may be substituted, or together represent an atomic group that forms a 5- or 6-membered ring containing 0 or 1 hetero atom with the nitrogen atom to which R1 and R2 are bonded; R3 represents a hydrogen atom, an alkyl group having 1 to 6 carbon atoms, a cycloalkyl group having 3 to 6 carbon atoms, an aryl group which may be substituted, or an arylalkyl group which may be substituted; and R4 represents an alkyl group having 1 to 6 carbon atoms, a cycloalkyl group having 3 to 6 carbon atoms, an aryl group which may be substituted, or an arylalkyl group which may be substituted;

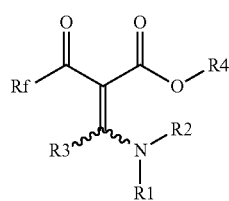
(3)

wherein Rf, R1, R2, R3 and R4 have the same definitions as above.

2. The method for producing a fluorine-containing acylacetic acid derivative according to claim 1, wherein R1 and R2 each independently represent an alkyl group having 1 to 6 carbon atoms or a cycloalkyl group having 3 to 6 carbon atoms, or together represent an atomic group that forms a 5- or 6-membered ring containing 0 or 1 hetero atom with the nitrogen atom to which R1 and R2 are bonded; R3 represents a hydrogen atom.

3. The method for producing a fluorine-containing acylacetic acid derivative according to claim 2, wherein Rf represents a trifluoromethyl group, R1 and R2 respectively represent a methyl group, and R4 represents an alkyl group having 1 to 6 carbon atoms.

4. A method for producing a fluorine-containing pyrazole-carboxylic acid ester derivative represented by the following Formula (5), comprising obtaining a mixture containing a base, a compound represented by the following Formula (1), and a compound represented by the following Formula (2), and adding a halogenating agent to the mixture:

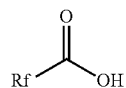
(1)

wherein Rf represents an alkyl group having 1 to 6 carbon atoms which is substituted by at least one fluorine atom;

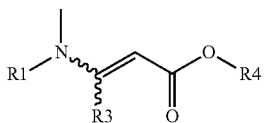
(2)

wherein R1 and R2 each independently represent a hydrogen atom, an alkyl group having 1 to 6 carbon atoms, a cycloalkyl group having 3 to 6 carbon atoms, an aryl group which may be substituted, an arylalkyl group which may be substituted, or an acyl group having 1 to 6 carbon atoms which may be substituted, or together represent an atomic group that forms a 5- or 6-membered ring containing 0 or 1 hetero atom with the nitrogen atom to which R1 and R2 are bonded; R3 represents a hydrogen atom, an alkyl group having 1 to 6 carbon atoms, a cycloalkyl group having 3 to 6 carbon atoms, an aryl group which may be substituted, or an arylalkyl group which may be substituted; R4 represents an alkyl group having 1 to 6 carbon atoms, a cycloalkyl group having 3 to 6 carbon atoms, an aryl group which may be substituted, or an arylalkyl group which may be substituted;

wherein Rf represents an alkyl group having 1 to 6 carbon atoms which is substituted by at least one fluorine atom;

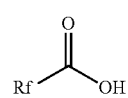 (1)

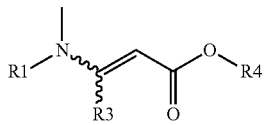 (2)

wherein R1 and R2 each independently represent a hydrogen atom, an alkyl group having 1 to 6 carbon atoms, a cycloalkyl group having 3 to 6 carbon atoms, an aryl group which may be substituted, an arylalkyl group which may be substituted, or an acyl group having 1 to 6 carbon atoms which may be substituted, or together represent an atomic group that forms a 5- or 6-membered ring containing 0 or 1 hetero atom with the nitrogen atom to which R1 and R2 are bonded; R3 represents a hydrogen atom, an alkyl group having 1 to 6 carbon atoms, a cycloalkyl group having 3 to 6 carbon atoms, an aryl group which may be substituted, or an arylalkyl group which may be substituted; and R4 represents an alkyl group having 1 to 6 carbon atoms, a cycloalkyl group having 3 to 6 carbon atoms, an aryl group which may be substituted, or an arylalkyl group which may be substituted;

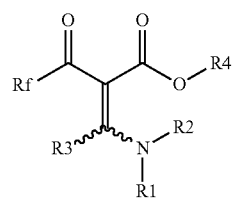 (3)

wherein Rf, R1, R2, R3 and R4 have the same definitions as above; reacting the compound represented by Formula (3) with a compound represented by the following Formula (4):

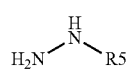 (4)

wherein R5 represents an alkyl group having 1 to 6 carbon atoms, a cycloalkyl group having 3 to 6 carbon atoms, an aryl group which may be substituted, or an arylalkyl group which may be substituted;

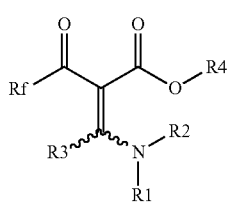 (3)

wherein Rf, R1, R2, R3 and R4 have the same definitions as above;

and reacting the compound represented by Formula (3) with a compound represented by the following Formula (4):

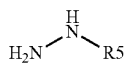 (4)

wherein R5 represents an alkyl group having 1 to 6 carbon atoms, a cycloalkyl group having 3 to 6 carbon atoms, an aryl group which may be substituted, or an arylalkyl group which may be substituted;

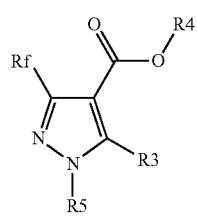 (5)

wherein Rf, R3, R4 and R5 have the same definitions as above.

5. The method for producing a fluorine-containing pyrazolecarboxylic acid ester derivative according to claim 4, wherein R1 and R2 each independently represent an alkyl group having 1 to 6 carbon atoms or a cycloalkyl group having 3 to 6 carbon atoms, or together represent an atomic group that forms a 5- or 6-membered ring containing 0 or 1 hetero atom with the nitrogen atom to which R1 and R2 are bonded; and R3 represents a hydrogen atom.

6. The method for producing a fluorine-containing pyrazolecarboxylic acid ester derivative according to claim 5, wherein Rf represents a trifluoromethyl group, R1 and R2 respectively represent a methyl group, R4 represents an alkyl group having 1 to 6 carbon atoms, and R5 represents an alkyl group having 1 to 6 carbon atoms.

7. A method for producing a fluorine-containing pyrazolecarboxylic acid derivative represented by the following Formula (6), comprising obtaining a mixture containing a base, a compound represented by the following Formula (1), and a compound represented by the following Formula (2), and adding a halogenating agent to the mixture:

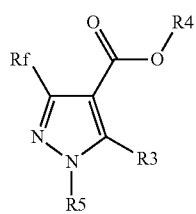
(5)

wherein Rf, R3, R4 and R5 have the same definitions as above;
and hydrolyizing the compound represented by Formula (5);

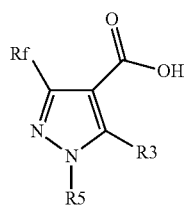
(6)

wherein Rf, R3, and R5 have the same definitions as above.

8. The method for producing a fluorine-containing pyrazolecarboxylic acid ester derivative according to claim 7, wherein R1 and R2 each independently represent an alkyl group having 1 to 6 carbon atoms or a cycloalkyl group having 3 to 6 carbon atoms, or together represent an atomic group that forms a 5- or 6-membered ring containing 0 or 1 hetero atom with the nitrogen atom to which R1 and R2 are bonded; and R3 represents a hydrogen atom.

9. The method for producing a fluorine-containing pyrazolecarboxylic acid ester derivative according to claim 8, wherein Rf represents a trifluoromethyl group R1 and R2 respectively represent a methyl group, R4 represents an alkyl group having 1 to 6 carbon atoms, and R5 represents an alkyl group having 1 to 6 carbon atoms.

* * * * *